US012409160B1

United States Patent
Granadino

(10) Patent No.: US 12,409,160 B1
(45) Date of Patent: Sep. 9, 2025

(54) COMPOSITIONS AND METHODS FOR TREATMENT OF PERI-IMPLANTITIS AND PERIODONTITIS

(71) Applicant: Cusp Biosciences, Inc., Chestnut Hill, MA (US)

(72) Inventor: Andrea Rosales Granadino, Revere, MA (US)

(73) Assignee: Cusp Biosciences, Inc., Lewes, DE (US)

( * ) Notice: Subject to any disclaimer, the term of this patent is extended or adjusted under 35 U.S.C. 154(b) by 0 days.

(21) Appl. No.: 19/212,445

(22) Filed: May 19, 2025

(51) Int. Cl.
| | |
|---|---|
| *A01N 43/00* | (2006.01) |
| *A01N 43/46* | (2006.01) |
| *A61K 9/00* | (2006.01) |
| *A61K 9/06* | (2006.01) |
| *A61K 31/277* | (2006.01) |
| *A61K 31/55* | (2006.01) |
| *A61K 47/10* | (2017.01) |
| *A61K 47/32* | (2006.01) |
| *A61K 47/36* | (2006.01) |
| *A61P 29/00* | (2006.01) |

(52) U.S. Cl.
CPC .......... *A61K 31/277* (2013.01); *A61K 9/0019* (2013.01); *A61K 9/06* (2013.01); *A61K 47/10* (2013.01); *A61K 47/32* (2013.01); *A61K 47/36* (2013.01); *A61P 29/00* (2018.01)

(58) Field of Classification Search
None
See application file for complete search history.

(56) References Cited

U.S. PATENT DOCUMENTS

2015/0328185 A1* 11/2015 Rosenberg Messina .................... A61K 31/366 548/537
2020/0397948 A1* 12/2020 Moshaverinia ......... A61L 27/26

FOREIGN PATENT DOCUMENTS

WO WO-2020211859 A1 * 10/2020 ........... A61K 9/0024

* cited by examiner

*Primary Examiner* — Layla Soroush
(74) *Attorney, Agent, or Firm* — Christopher Pilling

(57) ABSTRACT

Described are uses of hypoxia-inducible-factor-2 α (HIF-2α) inhibitors, e.g., belzutifan, for the local management of peri-implantitis, periodontitis and related inflammatory bone-loss conditions. Pharmaceutical compositions, kits, and other embodiments are also described.

4 Claims, No Drawings

COMPOSITIONS AND METHODS FOR TREATMENT OF PERI-IMPLANTITIS AND PERIODONTITIS

FIELD OF THE INVENTION

The present disclosure relates to pharmaceutical compositions and methods for the local treatment of inflammatory dental diseases, particularly peri-implantitis and periodontitis, using certain hypoxia-inducible-factor-2 α (HIF-2α) inhibitors such as belzutifan delivered in muco-adhesive gels, biodegradable inserts, or similar site-retentive dosage forms.

BACKGROUND

Peri-implantitis is a progressive, biofilm-driven inflammation that destroys peri-implant soft tissue and alveolar bone, threatening osseointegration and ultimately leading to implant failure. Once bone loss is established, conventional mechanical debridement and systemic antimicrobials achieve only limited pocket closure, and adjunctive regenerative procedures are unpredictable. Consequently, a great deal of effort has been devoted to local drug delivery platforms that can concentrate a therapeutic agent within the peri-implant pocket while sparing the patient systemic exposure.

Chronic periodontitis likewise arises from a polymicrobial biofilm that drives relentless, hypoxia-laden inflammation, culminating in destruction of the periodontal ligament and adjacent alveolar bone. Once deep pockets have formed, conventional scaling and root planing plus systemic antibiotics rarely halt progression. Transcriptomic profiling of advanced lesions reveals up-regulated HIF-2α, RANKL, and pro-inflammatory cytokines, underscoring a hypoxic, osteoclast-biased signaling axis.

New therapies are needed to interrupt this process. One early clinical direction borrowed from periodontology is the topical use of lipid-modifying agents: gels containing simvastatin or atorvastatin have been shown to lower pro-inflammatory cytokines and stimulate new bone formation when applied to periodontal defects (European Pat. Pub. EP 2887932 A2). These formulations demonstrated the merit of repurposing systemically approved small molecules for intra-oral indications, yet their mechanism-up-regulation of VEGF and other pro-angiogenic factors-addresses only one facet of peri-implant pathology.

Refinements in carrier technology soon followed. Researchers have developed shear-thinning, adhesive hydrogels that can be injected into a narrow periodontal or peri-implant crevice, flow under shear, and then rapidly recover viscosity to resist the constant outward flux of crevicular fluid, optionally cross-linking in situ to entrap stem cells or bioactive factors (U.S. Pat. Pub. US 2020/0397948 A1). Complementary efforts created thermoresponsive Pluronic® systems that remain liquid at room temperature yet form a semisolid depot at body temperature, enabling sustained release of agents such as simvastatin or Wnt agonists for a period of days (PCT Pat. Pub. WO 2020/211859 A1). These advances validate the feasibility of residence-time-enhanced local delivery but still center on pathways that stimulate angiogenesis or osteogenesis.

BRIEF DESCRIPTION OF THE INVENTION

The present disclosure recognizes that precise, low-dose topical or local delivery of belzutifan can silence the hypoxic cytokine cascade directly at the lesion, suppress osteoclastic attack, and permit re-establishment of a healthy peri-implant interface—without raising circulating drug levels above the anemia threshold.

Emerging molecular data highlight a distinct and under-addressed driver of peri-implant bone resorption: pathological hypoxia and sustained activation of hypoxia-inducible-factor-2 α (HIF-2α) in the inflammatory microenvironment. Overexpression of HIF-2α up-regulates RANKL, TNF-α and IL-1β, tipping the balance toward osteoclastogenesis and inhibiting reparative osteoblast activity. Systemic inhibition of HIF-α with belzutifan has already proven safe and effective in VHL-associated tumors, but its oral route incurs dose-limiting anemia, discouraging chronic off-label use for dental conditions. Furthermore inhibition of HIF-1 is expected to worse clinical outcomes.

The inventor has recognized that the >100-fold preference of belzutifan for HIF-2 over HIF-1 means it can silence the catabolic, RANKL-driven osteoclast and IL-6/IL-8 inflammatory cascade that accelerates bone loss, while sparing HIF-1-mediated angiogenesis and wound-healing essential for gingival regeneration.

Thus, in some aspects of the invention, belzutifan is formulated and delivered locally to the periodontal tissue for treatment or peri-implantitis or periodontitis. In some aspects, belzutifan is formulated in a muco-adhesive hydrogel or a biodegradable insert that maintains therapeutic concentrations at the implant surface over time but is eventually resorbed. Pre-clinical models can show meaningful reductions in RANKL/OPG ratio, probing depth, and radiographic bone loss compared with carrier-only controls, confirming that local HIF-2α inhibition addresses a mechanistic gap left by earlier angiogenic or antimicrobial approaches.

DETAILED DESCRIPTION OF THE INVENTION

Definitions

Unless otherwise indicated, the terms below shall have the following meanings when used in the specification, claims, and abstract. Singular forms include the plural and vice-versa unless the context clearly dictates otherwise. "Comprising," "containing," "including," and grammatical variants thereof are intended to be open-ended, non-exclusive terms (i.e., "including but not limited to"). For compositions, all percentages are by weight of the total composition unless expressly stated otherwise.

"Belzutifan" refers to the small-molecule hypoxia-inducible-factor-2 α inhibitor having the United States Adopted Name belzutifan (also known as MK-6482 or PT-2977; CAS No. 1672668-24-4), together with all crystalline or amorphous forms, stereoisomers, isotopic variants and any pharmaceutically acceptable salt thereof.

An "HIF-2α inhibitor" is any compound that reduces the transcriptional activity of hypoxia-inducible-factor-2 α (the EPAS1 gene product) in a recognized cell-based assay by at least about 25% at a concentration not exceeding 10 mM. Unless expressly limited, the term encompasses belzutifan and structurally unrelated antagonists that meet the stated criterion.

The expression "dental disease" means any pathological condition of the oral hard or soft tissues, including, but not limited to, peri-implantitis, peri-implant mucositis, gingivitis, periodontitis, apical periodontitis, alveolar osteitis, medication-related osteonecrosis of the jaw and inflammatory root-resorptive lesions.

More specifically, "peri-implantitis" denotes an infectious inflammatory process affecting the tissues surrounding an osseointegrated dental implant, characterized clinically by probing depths of 5 mm or greater and bleeding or suppuration on probing, and confirmed radiographically by progressive crestal bone loss of at least 2 mm after functional loading. "Periodontitis" refers to a chronic biofilm-mediated inflammation around natural dentition that results in attachment loss and alveolar bone destruction as classified by the 2017 World Workshop staging system.

"Topical administration" is direct application of a composition onto an external surface or into a cavity of the oral mucosa, such as a periodontal or peri-implant pocket, so that therapeutic effect is achieved locally and systemic absorption, if any, is incidental. The term does not encompass intentional oral, parenteral or other systemic routes.

The phrases "oral tissue" and "oral mucosa" include gingiva, peri-implant sulcus epithelium, buccal and palatal mucosa, sublingual mucosa and the periodontal ligament.

A material is "muco-adhesive" when it adheres to wet mucosal surfaces by hydrogen bonding, electrostatic interaction or polymer chain interpenetration to remain substantially in place for at least about thirty minutes under resting salivary flow. A material is "bio-resorbable" or "biodegradable" when it is broken down in vivo into non-toxic by-products that are eliminated via normal metabolic or excretory pathways within roughly one to twelve weeks after placement.

The term "polymeric matrix" denotes a three-dimensional network of natural or synthetic polymers (for example polycaprolactone, gelatin, poly(lactic-co-glycolic acid), chitosan, polycarbophil or alginate) that entraps or carries the active ingredient and determines the mechanical strength and release profile of an insert, film, fiber, gel or similar dosage form.

A release profile is "controlled-release" when at least half of the total belzutifan dose is liberated over more than six hours and the release rate deviates from ideal first-order kinetics by no more than approximately twenty percent under standard in-vitro conditions. "Sustained release" signifies that the belzutifan concentration at the target tissue remains within twenty-five percent of its peak level for a period of at least six hours, whereas "immediate release" signifies that not less than eighty percent of the dose is delivered within thirty minutes in aqueous medium at thirty-seven degrees Celsius.

An "insert" or "intra-gingival insert" is a pre-formed solid or semi-solid article dimensioned to fit into a periodontal or peri-implant pocket and comprising a biodegradable or muco-adhesive matrix that contains belzutifan for controlled local delivery. A "hydrogel" is a water-swollen cross-linked polymer system containing at least about seventy weight-percent water; it may be shear-thinning or in-situ gelling. A material is "thixotropic" when its viscosity reversibly decreases by at least an order of magnitude as shear rate rises from 0.1 to 10 s$^{-1}$ at 25° C.

"Crevicular fluid" is the serum-derived exudate found in the gingival or peri-implant sulcus, typically having a protein concentration of twenty to forty mg/ml and a flow rate of roughly 0.05 to 0.2 ml per minute per pocket in health. The "RANKL to OPG ratio" is the molar ratio between receptor activator of nuclear factor-κB ligand and its decoy receptor osteoprotegerin, measured for example by enzyme-linked immunosorbent assay.

An "effective amount" of belzutifan is a quantity sufficient to produce a measurable clinical improvement, such as at least a 1 mm reduction in probing depth, a 25% decrease in the RANKL/OPG ratio or a half-millimeter reduction in bone-loss progression, without unacceptable toxicity.

The terms "subject" and "patient" embrace human beings and, unless otherwise excluded, non-human mammals such as dogs, cats and horses. "Treatment" or "treating" covers therapeutic, prophylactic and maintenance interventions that prevent, alleviate, ameliorate, reverse or cure a disease or a symptom thereof, while "prophylaxis" or "preventing" refers to administration to an individual at risk but not yet manifesting clinical disease.

A "pharmaceutically acceptable carrier" is an excipient or mixture of excipients—water, glycerol, ethanol, polysorbates and the like—that is non-toxic, does not materially interfere with the activity of the active ingredient (e.g., belzutifan or salt or analog thereof) and is suitable for intra-oral delivery. A "dosage unit" is a physically discrete form containing a pre-determined amount of active ingredient intended for a single application. A "kit" is a packaged assembly comprising at least one such dosage unit and written instructions for use, and may include ancillary items such as applicator tips, irrigants or diagnostic strips.

Unless otherwise expressly described, "viscosity" refers to apparent viscosity measured with a rotational rheometer equipped with cone-and-plate geometry at the specified shear rate and temperature. A "thickening agent" or "viscosity modifier" is any excipient—such as polycarbophil, carbomer or fumed silica—that is added primarily to increase viscosity and thereby enhance mucosal retention.

"Pharmaceutically acceptable" indicates that the referenced substance meets recognized safety and purity standards for administration to humans or veterinary subjects.

These definitions are intended to aid in claim interpretation; however, the scope of the claims should not be limited by any example, embodiment, or preferred range expressly described herein, unless the claim so recites.

Active Ingredient

Belzutifan (Formula I) is a white-to-pale-yellow crystalline small molecule with a molecular weight of 383.34 g/mol:

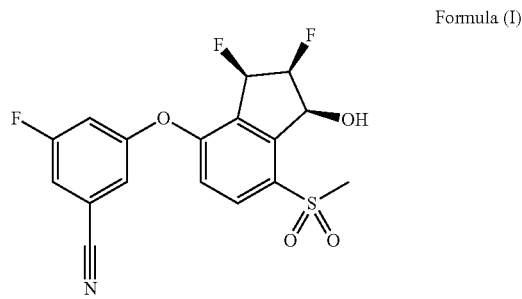 [SMILES: CS(=O)(=O)c1ccc(Oc2cc(F)cc(C#N)c2)c2c1[C@H](O)[C@H](F)[C@@H]2F]

Formula (I)

It contains a sulfone, a para-cyanophenoxy moiety and three vicinal fluorine atoms that impart both metabolic stability and lipophilicity (calculated log P≈4.1; topological polar surface area≈63 Å$^2$). The compound is practically insoluble in water across pH 1-8 and only sparingly soluble in ethanol, but is freely soluble in polar aprotic solvents such as DMSO (≈77 mg mL-1 at 25° C.). A single weakly basic sulfonamide nitrogen confers a predicted pK$_a$ of ~11.6, so the molecule is largely un-ionized under physiological conditions, yielding pH-independent low aqueous solubility.

Thermal analyses predict a melting/decomposition onset above 150° C. and a theoretical boiling point near 506° C., reflecting high lattice energy and oxidative robustness. Conversion to pharmaceutically acceptable salts enhances aqueous solubility by roughly two orders of magnitude, enabling formulation as muco-adhesive hydrogels and biodegradable inserts suitable for localized dental delivery as disclosed herein. In some embodiments, the concentration of belzutifan (or a pharmaceutically acceptable salt thereof) in the hydrogel is between 0.1% and 1%, inclusive, by weight of the total weight of the hydrogel. In some embodiments, the concentration of belzutifan (or a pharmaceutically acceptable salt thereof) in the hydrogel is between 0.3% and 0.7%, inclusive, by weight of the total weight of the hydrogel.

In some embodiments, the active ingredient is an analog of belzutifan or an acceptable salt thereof, provided that the active ingredient is an HIF-2α inhibitor. In some embodiments, the active ingredient is a compound of Formula II:

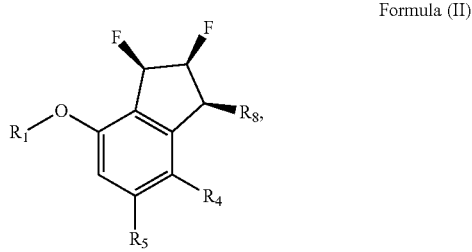

Formula (II)

or a pharmaceutically acceptable salt thereof, wherein:
$R_1$ is aryl or heteroaryl;
$R_4$ is halo, cyano, alkyl, sulfonamide, sulfinyl, sulfonyl or sulfoximinyl;
$R_5$ is hydrogen, halo or alkyl; and
$R_8$ is hydroxy, alkylamino, alkoxy or amino.

In some embodiments, $R_1$ is phenyl or pyridyl; and in some of those embodiments $R_8$ is hydroxy or amino. In some embodiments, the phenyl or pyridyl is substituted with at least one substituent selected from the group consisting of halo, C1-C4 alkyl, C1-C4 alkoxy, and cyano. In some embodiments, $R_4$ is cyano, fluoroalkyl, sulfonamide, sulfinyl, sulfonyl or sulfoximinyl. In some embodiments, $R_4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH) CF$_3$, —S(=O)(=N—CN)CH$_3$, —S(=O)(=N—CN)CH$_2$F, —S(=O)(=N—CN)CHF$_2$, and —S(=O)(=N—CN) CF$_3$.

In some embodiments, $R_5$ is hydrogen.

In some embodiments, $R_1$ is phenyl, monocyclic heteroaryl or bicyclic heteroaryl; and in some of those embodiments $R_4$ is cyano, fluoroalkyl, sulfonamide, sulfinyl, sulfonyl or sulfoximinyl; or $R_4$ is selected from the group consisting of —S(=O)$_2$CH$_3$, —S(=O)$_2$CH$_2$F, —S(=O)$_2$CHF$_2$, —S(=O)$_2$CF$_3$, —S(=O) 2NH$_2$, —S(=O)$_2$NHCH$_3$, —S(=O)(=N—CN)CH$_3$, —S(=O)(=N—CN)CH$_2$F, —S(=O)(=N—CN)CHF$_2$, and —S(=O)(=N—CN) CF$_3$; and in some of those embodiments $R_8$ is hydroxy or amino.

Various species within the scope of Formula (II) have been described, for example, in U.S. Pat. No. 9,969,689 B2 to Dixon et al. and are incorporated herein by reference for use in the present invention, each as an alternative to belzutifan. Where such a species is disclosed, use of any pharmaceutically acceptable salt thereof is also contemplated.

Furthermore, in any embodiment where belzutifan is used, it is understood that a pharmaceutically acceptable salt or analog of belzutifan can be substituted for belzutifan, provided that, in the case of an analog, the analog is an HIF-2α inhibitor.

Methods of Treatment

In one aspect, provided is a method of treating peri-implantitis in a subject, the method comprising topically administering to an oral tissue of the subject—preferably peri-implant soft tissue or the immediately adjacent crevicular sulcus—an effective amount of belzutifan or a pharmaceutically acceptable salt thereof.

In the context of peri-implantitis, "effective amount" means a quantity of belzutifan sufficient to achieve a clinically measurable improvement in at least one indicator of peri-implant health, such as reduction in probing depth, decrease in bleeding on probing, lowering of radiographic bone-loss progression, or a statistically significant reduction in the RANKL/OPG ratio in gingival crevicular fluid. In certain embodiments the effective amount yields a local belzutifan concentration of 0.05 µg/ml to 10 µg/ml at the tissue interface while maintaining systemic plasma levels below 5 ng/ml.

Administration is performed using a muco-adhesive carrier—for example, a hydrogel comprising chitosan, polycarbophil, or a combination thereof—so that the composition remains in contact with the peri-implant pocket for at least 30 minutes and preferably 4 to 24 hours. The hydrogel may further contain glycerol and water in a weight ratio of 1:3 to 1:6, and may be buffered to pH 5.5-7.0. In some embodiments, biodegradable microspheres such as poly(lactic-co-glycolic acid) (PLGA) particles are dispersed within the gel to provide sustained release of belzutifan over 24-72 hours.

The method can be carried out as a single application or as a repeating regimen, e.g., once daily for 5 to 30 consecutive days, depending on disease severity. Application may be accomplished with a blunt periodontal-tip syringe, a single-dose applicator, or by placing a pre-formed biodegradable insert dimensioned to fit within the peri-implant pocket (e.g., a ribbon measuring approximately 1 mm×2 mm×6 mm) in its flattened, unfolded, relaxed state.

Optionally, the method further comprises irrigation of the pocket with an antimicrobial rinse-such as 0.12 wt % chlorhexidine gluconate-immediately before each application. Systemic hematologic parameters (e.g., hemoglobin concentration) may be monitored, and treatment may be discontinued if hemoglobin decreases by more than 1.0 g/dl.

Patient Population and Identification of Candidates for Treatment

Eligible subjects. In some embodiments, candidates for therapy comprise human adults and adolescents (>16 years old) who present with at least one osseointegrated dental implant exhibiting clinical and radiographic signs of peri-implantitis, defined as: (i) probing depth (PD) ≥5 mm at ≥1 site on the implant; (ii) bleeding and/or suppuration on probing; and (iii) >2 mm of radiographic marginal-bone loss relative to the most coronal portion of the implant threads occurring after functional loading. The invention is also suitable for patients with moderate periodontitis (Stage II-III) affecting natural dentition, particularly when lesions are localized and accessible for site-specific application.

Diagnostic work-up. Assessment prior to treatment includes peri-implant PD charting, Modified Plaque Index, Gingival Index, full-mouth periapical or bite-wing radiographs, and (when available) cone-beam CT to quantify three-dimensional bone loss. Gingival-crevicular-fluid (GCF) samples may be collected to measure RANKL/OPG ratio and pro-inflammatory cytokines (IL-1β, TNF-α) as pharmacodynamic baseline markers. Systemic laboratory tests-complete blood count (CBC), serum ferritin, and comprehensive metabolic panel-establish hematologic and hepatic function in anticipation of belzutifan exposure, albeit minimal.

Risk-Stratification Factors

High-risk implant sites: implants positioned <3 mm from adjacent tooth roots or vital structures, or with suboptimal soft-tissue thickness (<2 mm keratinized mucosa), are prioritized because surgical access is limited.

Systemic modifiers: uncontrolled diabetes mellitus (HbA1c>8%), current smoking (>10 cigarettes/day), chronic corticosteroid or bisphosphonate use, and genetic polymorphisms increasing RANKL expression justify early-intervention use of the disclosed composition to arrest bone loss.

Inclusion Criteria Examples

| Criterion | Threshold | Rationale |
| --- | --- | --- |
| Probing depth | ≥5 mm | Indicative of pathologic pocket needing local drug delivery |
| Radiographic bone loss | ≥2 mm vs. baseline | Confirms progressive peri-implantitis |
| Bleeding on probing | Present at ≥2 sites | Surrogate for active inflammation |
| Hb concentration | ≥11.0 g dl$^{-1}$ | Provides margin against belzutifan-related anemia, even at low systemic exposure |

Exclusion Criteria Examples

Pregnancy or lactation (belzutifan Category D systemically; precaution maintained for local use).

Hemoglobin <11 g/dL or symptomatic iron-deficiency anemia.

Known hypersensitivity to belzutifan or formulation excipients.

Untreated oral mucosal infections (e.g., candidiasis, herpetic stomatitis) that could confound safety readouts.

Previous peri-implant surgery at the target site within 90 days.

Patient counseling and monitoring. All candidates receive oral-hygiene instruction and non-surgical debridement before first application. During treatment, PD, bleeding index, and GCF biomarkers are re-evaluated at weeks 2, 4, and 8. CBC is repeated at week 4; treatment guidelines recommend discontinuation when hemoglobin falls by >1.0 g/dl or ferritin drops below 30 ng/ml. Standard radiographic follow-up at 6 and 12 months documents stabilization or gain of crestal bone height.

Other Indications

While peri-implantitis is the primary indication, the same patient-selection principles extend to: (i) early peri-implant mucositis where pocket depth is 4 mm but bleeding persists despite debridement; (ii) localized aggressive periodontitis in young adults carrying specific JP2 clone *Aggregatibacter actinomycetemcomitans*; and (iii) furcation defects of molars where surgical access is compromised.

In addition to peri-implantitis, the topical belzutifan compositions described herein are suitable for treating various forms of periodontitis and a variety of hypoxia-driven or osteoclastic dental disorders, including: (i) peri-implant mucositis, where efficacy can be gauged by reduction in modified bleeding-on-probing (mBOP) scores and mucosal redness index; (ii) chronic or aggressive periodontitis affecting natural dentition, measurable as a ≥1 mm gain in clinical attachment level and ≥0.5 mm radiographic bone fill over 6 months; (iii) apical periodontitis or radicular cysts, tracked by ≥30% decrease in periapical radiolucency diameter on CBCT imaging; (iv) external cervical or orthodontic root resorption, assessed by diminution of resorptive lacunae depth or volume on serial radiographs; (v) medication-related osteonecrosis of the jaw (MRONJ) in its early stages, where success corresponds to complete mucosal coverage of previously exposed bone and elimination of suppuration; and (vi) post-extraction socket healing or alveolar osteitis ("dry socket"), for which accelerated soft-tissue epithelialization and ≥25% increase in trabecular bone density at 8 weeks serve as endpoints. In some embodiments, the patient to be treated has any one, any combination of, or even all of the foregoing conditions, and topical HIF-2α inhibition with belzutifan is administered to address each such disease state concurrently. In each case, a pharmaceutically acceptable salt of belzutifan analog may be used for treatment of the same conditions, as described herein.

Method of Administration

The following protocol is intended for use by a dentist, periodontist, or dental hygienist. Steps are written presuming the muco-adhesive gel embodiment; minor adjustments for the biodegradable insert are noted parenthetically.

Pre-Treatment Preparation

| Task | Detail |
| --- | --- |
| Clinical debridement | Supra- and sub-gingival mechanical debridement using titanium curettes or ultrasonic tips (≤1 mm tip diameter) to disrupt biofilm on implant surfaces. |
| Pocket irrigation | Rinse the peri-implant pocket with 5-10 ml sterile saline; optionally follow with 1 ml of 0.12% chlorhexidine gluconate, dwell 60 s, suction clear. |
| Isolation and dryness | Gently air-dry the pocket entrance; place cotton rolls or use cheek retractors to limit salivary ingress. Local anesthetic is generally unnecessary but 2% lidocaine without epinephrine may be infiltrated if the site is sensitive. |
| Baseline recording | Confirm probing depth (PD), bleeding on probing (BOP), and pocket geometry to calculate required gel volume (~0.02 mL mm$^{-1}$ PD). |

Gel Application

Load applicator—Use a pre-filled 1 ml luer-lock syringe fitted with a 25-27 G blunt, side-ported periodontal cannula (diameter≤0.5 mm).

Cannula insertion—Insert cannula to base of pocket (until gentle resistance is felt), keeping the side-port oriented toward the implant surface.

Delivery while withdrawing—Depress plunger steadily while withdrawing cannula coronally, filling the pocket from apical to coronal extent; typical dose 0.05-0.20 ml per site.

Surface smear—Express a thin film over the gingival margin to enhance seal.

Setting period—Maintain isolation for 3 minutes to allow initial viscosity recovery; instruct patient to refrain from rinsing, eating, or drinking for 30 minutes.

(For the insert embodiment, place a pre-formed ribbon—1×2×6 mm into the pocket using cotton pliers until flush with gingival margin; no gel sealing required.)

Post-Application Instructions

| Timeframe | Patient guidance |
|---|---|
| 0-30 min | Do not rinse, spit, eat, or drink. Passive swallowing is acceptable. |
| 30 min-4 h | Soft diet; avoid hot beverages and vigorous swishing. |
| 24 h | Resume normal oral hygiene except avoid interproximal brushes or floss at treated site. Instead, gently wipe the margin with a cotton-tipped applicator moistened in 0.05% cetylpyridinium chloride. |

Dosing Schedule

| Disease severity (initial PD) | Dosing frequency | Duration |
|---|---|---|
| 5-6 mm | Once daily | 5 days |
| 7-8 mm | Once daily | 10 days |
| ≥9 mm or circumferential defect | Once daily | 15 days |

Each daily dose is a fresh application following the same debridement-light irrigation-dry-deliver sequence. For the insert embodiment, replace insert at 72-hour intervals.

Follow-Up and Retreatment Criteria

| Visit | Measurements | Action |
|---|---|---|
| Week 2 | PD, BOP, GCF RANKL/OPG | If PD decrease ≥ 1 mm and BOP reduced, continue planned course; otherwise extend treatment by 5 days. |
| Week 4 | PD, BOP, CBC (hemoglobin) | Discontinue if Hb drop > 1 q dL$^{-1}$. If PD still ≥ 5 mm, consider a second treatment cycle after 2 weeks rest. |
| Month 3 and 6 | PD, radiograph | If bone loss halted and PD ≤ 4 mm, transition to maintenance; if progression evident, evaluate for surgical intervention. |

Special Considerations

Multiple implants—Treat a maximum of two sites per quadrant per session to limit accidental swallowing of gel.

Adjunctive antimicrobials—Systemic antibiotics are not routinely required; if prescribed (e.g., amoxicillin+metronidazole), begin 24 h after gel therapy starts to avoid pH disruption.

Systemic exposure safeguards—The applied gel volume (<1 ml total) delivers <5 mg belzutifan, yielding predicted Cmax <5 ng/ml; nonetheless, advise patients to report fatigue or dyspnea.

Pregnancy—Defer treatment until postpartum unless the risk of implant loss outweighs theoretical teratogenicity; confirm negative pregnancy test in women of child-bearing potential.

This administration protocol ensures the composition is accurately placed, retained for a therapeutically relevant interval, and reapplied on a regimen matched to lesion severity, thereby providing full practical support for the claimed method of treating peri-implantitis with topical belzutifan.

Pharmaceutical Composition

In another aspect, provided is a pharmaceutical composition suitable for topical intra-oral delivery, comprising:

Active ingredient. Belzutifan (or analog) or a pharmaceutically acceptable salt thereof present at 0.01 wt % to 5 wt %, more preferably 0.1 wt % to 1 wt % based on the total weight of the composition. The drug may be supplied as a micronized powder (D90≤10 μm) or pre-dissolved in a pharmaceutically acceptable co-solvent such as 10% v/v ethanol or 5% v/v polyethylene glycol 400 before incorporation into the bulk matrix.

Muco-adhesive carrier. A bio-resorbable polymer system selected from chitosan, polycarbophil, or a combination thereof at 1 wt % to 6 wt % total polymer. Chitosan may be deacetylated to 75-95% and neutralized with sodium β-glycerophosphate to impart pH-sensitive gelling. Polycarbophil provides carbomer-like viscosity and strong hydrogen-bonding to mucins. In certain embodiments, the carrier additionally contains glycerol and water in a weight ratio of 1:3 to 1:6, providing both humectancy and plasticity.

Optional viscosity modifiers and secondary muco-adhesives. The formulation may further include sodium alginate or hyaluronic acid (0.1 wt %-2 wt %) to enhance retention time and tissue comfort. These polysaccharides interpenetrate with chitosan/polycarbophil networks to form an interpolymer complex that resists dilution by gingival crevicular fluid.

Exemplary thixotropic and rheological properties. The fully hydrated composition exhibits thixotropic behavior, possessing a static viscosity of 5,000 cP to 50,000 cP measured at a shear rate of 0.1 s$^{-1}$ (25° C.), and dropping by at least one order of magnitude when shear is increased to 10 s$^{-1}$, thereby allowing facile injection yet rapid recoalescence to a viscous depot once shear is removed. In some embodiments, the composition has a viscosity of 5,000 cP to 30,000 cP measured at a shear rate of 1 s$^{-1}$ (25° C.). In some embodiments, the composition has a viscosity of less than 1,000 cP at 100 s$^{-1}$. In some embodiments, 0.15 ml of the hydrogel passes through a 23-gauge sub-gingival cannula under a thumb force of ≤20 N.

Exemplary buffer system and pH. A citric-acid/phosphate buffer adjusts the formulation to pH 6.0±0.5, a range compatible with oral tissues and the solubility profile of belzutifan. Buffer strength may be 5-20 mM to maintain pH during the residence period but permit eventual physiological equilibration.

Sustained-release micro-reservoirs (optional). In certain embodiments, belzutifan is co-encapsulated within biodegradable PLGA microspheres (50:50 lactide: glycolide, inherent viscosity 0.4-0.6 dl/g). Microspheres range from 1 μm to 50 μm in diameter, carry 5 wt %-20 wt % drug loading, and are dispersed at 0.5 wt %-5 wt % of the total gel. In vitro release testing (USP apparatus 4, simulated crevicular fluid, 37° C.) demonstrates zero-order kinetics delivering 0.1 μg to 2 μg belzutifan per day over 24 h to 72 h, matching the pharmacodynamic window needed to downregulate RANKL expression without systemic accumulation.

Exemplary Manufacturing Process.

a. Step 1—Polymer hydration: Chitosan is dispersed in deionized water, acidified to pH 4.0 with lactic acid, and allowed to swell for >2 h at ambient temperature.

b. Step 2—Active incorporation: Micronized belzutifan is suspended (or drug-in-solution added) under high-shear mixing; if microspheres are employed, they are folded in gently with a planetary mixer to avoid polymer fracture.

c. Step 3—pH adjustment and buffering: Sodium β-glycerophosphate or triethanolamine gradually elevates pH to 5.5-6.0, followed by addition of the citric/phosphate buffer.

d. Step 4—Homogenization and deaeration: The bulk is passed through a rotor-stator homogenizer (3 min, 3,000 rpm) and vacuum-deaerated to remove entrained air, yielding a smooth, injectable hydrogel.

e. Step 5—Aseptic filling: The gel is filled into 1 mL luer-lock syringes fitted with blunt periodontal tips or into single-dose thermoform blister reservoirs under Class 100 laminar-flow conditions, then terminally sterilized by γ-irradiation (15 kGy) or aseptically manufactured, depending on polymer stability.

Packaging and shelf life. Finished product is stored at 2° C. to 8° C., protected from light and oxygen. Accelerated stability (40° C./75% RH) for six weeks projects a refrigerated shelf life of 24 months, with belzutifan potency loss <5%.

Excipients

The topical and intra-gingival dosage forms of the invention may include one or more pharmaceutically acceptable excipients drawn from the functional categories set out below. Unless the context dictates otherwise, the named substances are illustrative and not limiting, and any individual excipient may be employed alone or in any combination to achieve the desired physical, chemical, microbiological or organoleptic properties.

Muco-adhesive and viscosity-building polymers. To confer tissue adherence and the gel-like rheology needed for pocket retention, the composition may contain hydrophilic polymers such as chitosan (typically 0.2-4% w/w for gels, or 10-30% w/w for inserts), polycarbophil or carbomer (for example Carbopol 974P at about 0.1-1%), hyaluronic acid or sodium alginate (usually 0.05-2%), pectin, gellan gum, xanthan gum, pullulan or guar gum. Where a thermoresponsive profile is desired, poloxamers such as Poloxamer 407 or 188 (5-30%) or methylcellulose/hydroxypropyl-methylcellulose (roughly 1-4%) may be incorporated to afford shear-thinning or sol-to-gel transition behavior.

Structural biodegradable polymers for solid inserts and films. Polycaprolactone, poly(lactic-co-glycolic acid) (PLGA), poly-1-lactic acid, polyethylene oxide, gelatin, silk fibroin and polyvinyl alcohol may together or individually form the bulk matrix of an insert, usually at loadings of 20-90% of the finished mass depending on density and porosity requirements.

Plasticizers, humectants and co-solvents. Glycerol, propylene glycol, triethylene glycol, polyethylene glycol 400, sorbitol solution, xylitol and triethyl citrate (each typically 1-25%) soften the polymer network, reduce brittleness, improve spreadability and aid water retention. Small amounts of ethanol (5-20% v/v), isopropyl alcohol ($\leq$10% v/v) or N-methyl-2-pyrrolidone may be used as co-solvents during processing but are usually removed or reduced to residual levels during drying.

Buffer systems and pH modifiers. Citrate, phosphate, acetate, lactate or TRIS buffers in the range of 5-50 millimolar adjust and maintain the pH typically between 5.0 and 7.5; sodium β-glycerophosphate or triethanolamine may be added incrementally to neutralize acidic polymers such as chitosan.

Surfactants and wetting agents. To aid dispersion of belzutifan or to improve wettability, non-ionic surfactants such as polysorbate 80 or 20, poloxamer 188, lecithin or amphiphilic phospholipids can be employed at low levels (about 0.01-3%). Anionic surfactants such as sodium lauryl sulfate are feasible but are generally limited to $\leq$0.2% to minimize mucosal irritation.

Preservatives and antimicrobial stabilizers. Single-dose, terminally sterilized presentations often require no preservative, yet multi-dose gels may incorporate methyl- or propyl-paraben, benzyl alcohol, phenoxyethanol, sodium benzoate, potassium sorbate, chlorhexidine digluconate or cetylpyridinium chloride in amounts ranging from roughly 0.05-1% as permitted by regional pharmacopeias.

Antioxidants and chelators. Butylated hydroxytoluene, butylated hydroxyanisole, sodium metabisulfite, ascorbic acid or disodium EDTA (typically 0.005-0.1%) may be added to inhibit oxidative degradation of belzutifan in high-surface-area dosage forms such as electrospun fibers.

Tonicity adjusters and mineral salts. For mouth-rinse or spray embodiments, isotonicity can be achieved with sodium chloride, potassium chloride, mannitol or calcium chloride in the approximate range of 0.1-0.9%.

Flavors, sweeteners and coloring agents. Peppermint or spearmint oils, menthol, sucralose, acesulfame-K, stevia extract, erythritol and—for esthetic purposes—titanium dioxide or pharmaceutically acceptable FD&C dyes may be used sparingly (flavors 0.01-0.5%, sweeteners 0.1-2%, colors 0.001-0.5%), particularly in dosage forms expected to contact the broader oral cavity, such as buccal films or rinses.

Porosity modifiers and bulking agents. Microcrystalline cellulose, lactose monohydrate, mannitol (spray-dried), calcium phosphate or sodium starch glycolate can fill void space and tailor mechanical strength in solid inserts, commonly at 5-60% of the insert mass.

Cross-linking or in-situ gelling reagents. Genipin, low-ppm glutaraldehyde, ionic calcium (for alginate systems) or enzymatic transglutaminase can be provided stoichiometrically relative to reactive polymer groups to create a denser network after placement.

All excipients are selected from materials generally recognized as safe or described in the current editions of the United States Pharmacopeia (USP), the European Pharmacopoeia (Ph. Eur.) or equivalent compendia, and are included in grades suitable for mucosal administration. The broad catalogue set forth above supplies an ample written-description basis for any future amendment that substitutes, adds or deletes excipients in response to manufacturing, regulatory or clinical constraints encountered during prosecution or commercial scale-up.

General Guidance

Excipients should be USP/NF, Ph. Eur., JPE, or comparable pharmacopeial grade.

Concentrations may vary outside the recited ranges when functionally justified (e.g., high-plasticizer loads for freeze-thaw stability).

Surfactant levels should be minimized to reduce mucosal irritation (<CMCs where possible).

Preservatives are optional in single-dose, terminally sterilized presentations.

Flavors, sweeteners, and colors are generally omitted from intra-gingival inserts but may be desirable in gels intended for widespread intra-oral contact.

In certain embodiments the belzutifan (or analog) content (expressed as weight percent of the total composition) may be selected from the following graduated ranges, each lower limit being combinable with any higher limit to define still-narrower sub-ranges as desired during prosecution: about 0.0001 wt % to 0.001 wt %; 0.0005 wt % to 0.005 wt %; 0.001 wt % to 0.01 wt %; 0.005 wt % to 0.05 wt %; 0.01 wt % to 0.1 wt %; 0.05 wt % to 0.5 wt %; 0.1 wt % to 1 wt %; 0.5 wt % to 2 wt %; 1 wt % to 5 wt %; 2 wt % to 10 wt %; 5 wt % to 15 wt %; and 10 wt % to 20 wt %.

Biodegradable Intra-Gingival Insert

The insert is a self-retaining, biodegradable ribbon or rod that fits within a peri-implant or periodontal pocket and delivers belzutifan locally for 3-14 days, after which the matrix resorbs into biocompatible by-products. It is engineered to (i) withstand crevicular-fluid flow, (ii) release drug at 0.1-2 µg/day, and (iii) maintain intimate contact with soft tissue The biodegradable intra-gingival insert is formed from a multiphase polymeric matrix in which a slowly eroding, semicrystalline polycaprolactone (PCL) backbone is intimately blended with faster-hydrating, hydrophilic domains to achieve both structural integrity and controlled drug release. In a representative formulation, between about 55 and 75% w/w of the finished insert is PCL having a number-average molecular weight of roughly 80 kDa; this component supplies tensile strength, shape retention and the long-term barrier that extends drug liberation beyond one week. Gelatin, preferably type B with a bloom value of 225, is incorporated at about 15 to 25% w/w. Upon implantation the gelatin rapidly absorbs crevicular fluid, swells and creates aqueous channels that facilitate belzutifan diffusion while simultaneously providing a muco-adhesive outer surface that anchors the insert against the pocket wall. To fine-tune the overall degradation rate, poly(lactic-co-glycolic acid) (PLGA) having a 75:25 lactide-to-glycolide ratio and an inherent viscosity near 0.45 dl/g is added in an amount ranging from 5 to 25% w/w. As the PLGA domains hydrolyze they generate microscale pores and acidic by-products, thereby accelerating water ingress into the PCL phase and preventing the otherwise abrupt loss of mechanical integrity that pure gelatin swells might produce.

The active ingredient, belzutifan (or analog) or a pharmaceutically acceptable salt thereof is uniformly dispersed throughout the matrix at a loading of approximately 0.5 to 10 mg/mm$^3$, corresponding to about 0.5 to 10% w/w depending on the density of the final insert. In some embodiments, the concentration of belzutifan (or a pharmaceutically acceptable salt thereof) in the intra-gingival insert is between 1% and 10%, inclusive, by weight of the total weight of the hydrogel. In some embodiments, the concentration of belzutifan (or a pharmaceutically acceptable salt thereof) in the intra-gingival insert is between 3% and 7%, inclusive, by weight of the total weight of the hydrogel. Drug particles are cryo-milled to a median diameter below five micrometers—or are pre-entrapped in PLGA microspheres—so that release follows a combined diffusion-and-erosion mechanism rather than surface wash-off. A small quantity—typically 1 to 5% w/w—of a biocompatible plasticizer such as triethyl citrate or polyethylene glycol 400 is included to lower the glass-transition temperature of the polymer blend, imparting sufficient flexibility for chair-side insertion without fracturing.

When prepared as a ribbon measuring roughly 1 mm×2 mm in cross-section and 6 mm in length in its flattened, unfolded, relaxed state, the described matrix offers an ideal balance: it is firm enough to be advanced to the apical extent of a periodontal or peri-implant pocket, yet pliant enough to conform to the irregular inner surface. In simulated crevicular fluid held at 37° C. the insert absorbs ten to twenty percent of its mass in water within the first hour, releases less than ten percent of its belzutifan payload during that period, and thereafter delivers the drug in a near-zero-order fashion—typically between 0.1 and µg/day—for a duration of 3 to 14 days. By day 28, controlled in-vitro degradation testing shows that at least 90% of the original mass has resorbed into non-toxic lactic, glycolic and ¿-caprolactone oligomers together with benign gelatin peptides, all of which are cleared by normal metabolic pathways.

Optional variants may substitute part of the PCL with poly-1-lactic acid for a stiffer matrix, replace gelatin with a chitosan-derived polysaccharide to enhance antibacterial properties, or incorporate bioactive ceramic fillers such as hydroxyapatite in amounts up to ten percent to promote hard-tissue integration.

Exemplary Geometry and Physical Properties
  Preferred dimensions: 1 mm×2 mm cross-section; length 6 mm (variant lengths 3-10 mm).
  Mass: 5-15 mg per insert (~ 0.2-0.6 ml pocket volume displacement).
  Flexural modulus (ASTM D790, 37° C., hydrated): 20-60 MPa-adequate to push insert apically while conforming to pocket curvature.
  Muco-adhesive force (texture analyzer, porcine gingiva): ≥0.15 N after 60 s contact.
Exemplary Drug-Release Kinetics
  In-vitro method: USP Apparatus 4, 37° C., flow-through cell, simulated crevicular fluid (pH 7.4).
  Profile: Burst <10% in first 2 h; quasi-zero-order thereafter, cumulative release 70-90% by day 14.
  Mechanism: Combination of diffusion through hydrated gelatin channels and erosion of PLGA domains exposing PCL lamellae.
Exemplary Biodegradation
  Weight loss (37° C. PBS, pH 7.4):
  20-35% at day 7
  55-80% at day 14
  ≥90% at day 28 (residual PCL fragments <50 µm spontaneously exfoliate and are expelled or phagocytosed).
  Degradation products: Lactic acid, glycolic acid, ¿-caprolactone oligomers, and gelatin peptides—all resorbed via normal metabolic pathways.
  pH modulation: PLGA content capped at 20 wt % to prevent acidic microenvironment; in-situ pH never falls below 6.4.
Exemplary Manufacturing Process (Solvent-Casting and Lamination Example)
  Polymer solution A: Dissolve PCL in 1,4-dioxane (12% w/v) at 45° C.
  Polymer solution B: Disperse gelatin in water/ethanol (60:40) at 45° C., add triethyl citrate.
  Active phase: Suspend micronized belzutifan (D90≤5 µm) into Solution B under high-shear (5,000 rpm, 3 min).
  Blend: Combine Solutions A and B (3:1 v/v) with PLGA microparticles (d50≈10 µm) under nitrogen.
  Casting: Doctor-blade cast the mixture (250 µm wet-thickness) onto PTFE substrate in <10% RH dry room.
  Solvent removal: Vacuum-dry 16 h (40° C., ≤30 mbar) to residual solvent <500 ppm.
  Lamination and slitting: Thermally laminate two films at 55° C. under 0.2 MPa to achieve 500 µm final thickness; slit into 1×2 mm ribbons, die-cut to 6 mm length.
  Sterilization: Ethylene oxide (EO)$_{12}$% at 45° C., 2 h exposure; residual EO <10 ppm after 72 h aeration.
  Alternative processes include hot-melt extrusion (PCL/PLGA masterbatch with belzutifan at 80° C.), and electrospinning of coaxial fibers followed by thermocompression to consolidate into a ribbon.
Packaging and Storage
  Primary pack: Teflon-coated carrier card in Type I glass vial (13 mm crimp), nitrogen-flushed, silica gel desiccant.
  Secondary pack: Aluminum-polyester-polyethylene sachet with temperature indicator.
  Shelf-life: Real-time stability at 25° C./60% RH projects 24 months (potency loss <5%, no change in tensile properties).
Insertion Technique
  Debride and irrigate pocket; gently dry.
  Grasp insert with cotton pliers; advance apically along implant surface until flush with gingival margin.
  Apply light digital pressure 5 s to enhance muco-adhesion; no suturing required.

Replace insert every 72 h for severe lesions (>8 mm PD) or allow full resorption for moderate lesions (≤7 mm PD).

Safety and Biocompatibility

Cytotoxicity (ISO 10993-5, L-929): >90% cell viability.

Sensitization (Murine LLNA): Stimulation index <2.

Systemic toxicity (ISO 10993-11, rat, 14 days): No clinical signs, normal CBC and liver enzymes.

For solid or semi-solid inserts, suitable loadings span 0.01 µg/mm³ to 0.1 µg/mm³; 0.05 µg/mm³ to 0.5 µg/mm³; 0.1 µg/mm³ to 1 µg/mm³; 0.5 µg/mm³ to 5 µg/mm³; 1 µg/mm³ to 10 µg/mm³; 5 µg/mm³ to 25 µg/mm³; and 10 µg/mm³ to 50 µg/mm³.

Alternative Dosage Forms

While site-retentive muco-adhesive gels and biodegradable pocket inserts represent preferred embodiments, the invention is not limited to these. The following alternative dosage forms provide additional formulation flexibility, clinical convenience, and other advantages. Each can incorporate belzutifan (or analog) or a pharmaceutically acceptable salt in any concentration range disclosed elsewhere, optionally together with one or more excipients listed in the Excipients Menu.

Buccal or sublingual films. In one embodiment the drug is incorporated into a thin, flexible film, typically 50-150 µm thick, composed of a hydrophilic matrix such as hydroxypropyl-methylcellulose or polyvinyl alcohol plasticized with glycerol. The film—loaded with belzutifan at roughly 0.1-mg/cm²—is pressed against the buccal or sublingual mucosa, where saliva hydrates the polymer and causes it to adhere and dissolve over five to thirty minutes, bathing the entire dentition in drug-laden saliva. This format is especially convenient for patients who require multi-site coverage or who prefer a discreet, self-administered dosage unit.

Electrospun nanofiber mats. Alternatively, belzutifan may be entrapped in an electrospun mat of sub-micron fibers composed, for example, of a polycaprolactone/gelatin blend. The resulting non-woven mesh, usually half a millimeter to one millimeter thick, can be trimmed chair-side and tucked around an implant cuff or into an infrabony defect. Upon hydration the gelatin component swells, while the high surface area of the fibers permits an initial burst followed by sustained release; the mat gradually disintegrates over seven to fourteen days.

In-situ forming injectable depots. A further option employs a low-viscosity solution of PLGA (15-30% w/w) and belzutifan dissolved in N-methyl-2-pyrrolidone or a similar biocompatible solvent. Injected through a 30-gauge needle to the base of the periodontal or peri-implant pocket, the solution encounters crevicular fluid, whereupon the solvent diffuses out and the polymer precipitates, forming a coherent depot that erodes over two to four weeks without the need for subsequent removal.

Bio-adhesive varnishes. For lesions confined to exposed implant threads or cervical root surfaces, belzutifan may be formulated in an ethylcellulose-based varnish containing ethanol and a small amount of shellac. The liquid is painted onto the target area with a micro-brush; as the solvent evaporates it leaves behind a transparent, adherent film that slowly releases the drug while allowing visual inspection.

Liposomal mouth-rinse concentrate. In another embodiment the active is encapsulated within unilamellar soy-phosphatidylcholine/cholesterol liposomes (average diameter about nm), suspended in an isotonic, flavored aqueous base. The patient swishes ten ml for 60 seconds twice daily. Liposomes penetrate the gingival sulcus and fuse with epithelial membranes, offering a non-invasive maintenance therapy after an initial professional course.

Chewing gum or pastilles. Belzutifan can also be incorporated into a xylitol-based chewing gum or a gelatin pastille. A single unit containing 5 to 10 mg of drug is chewed for 5 to 10 minutes, releasing belzutifan into saliva while stimulating salivary flow and distribution. Such self-dosing aids compliance and doubles as a caries-preventive xylitol chew.

Ion-exchange resin complexes. Taste masking and near-zero-order release are attainable by binding belzutifan hydrochloride to micro-beads of a cation-exchange resin such as Amberlite IRP-64. The resin is dispersed into the gel or film; once placed, sodium and potassium ions in crevicular fluid gradually displace the drug from the resin matrix, yielding a controlled release lasting 48 hours or more.

Three-dimensional printed biodegradable cones. For post-extraction sockets or deep intra-bony defects, the drug may be blended into a poly-1-lactic-acid or polycaprolactone filament and printed into a tapered cone—typically 0.5 to 1.5 mm in diameter and 5 to 10 mm long—using fused-deposition modeling. The cone is inserted into the socket where it softens and resorbs over 2 to 3 weeks, providing custom geometry and sustained delivery.

Thermo-reversible sprays. A still lighter-weight alternative is a chilled, low-viscosity solution of Poloxamer 407 (about 15%) containing belzutifan. When the clinician sprays 1 to 2 ml onto the gingiva, body heat converts the liquid into a viscous gel that coats a broad mucosal surface and dissolves slowly, making it attractive for post-surgical anti-inflammatory coverage.

Bio-adhesive micro-tablet pellets. Finally, the drug may be compressed with chitosan, lactose and a lubricant into 1 to 2 mm pellets. A single pellet (approximately one milligram of belzutifan) is dropped into a periodontal pocket, where exposure to crevicular fluid causes slight swelling and muco-adhesion; the pellet erodes over 3 to 5 days, after which a fresh pellet can be placed if required.

In every instance the alternative dosage form is engineered to deliver belzutifan at a locally therapeutic level—typically maintaining concentrations of about 0.05 to 0.5 µg/ml in the surrounding tissue—while keeping systemic plasma levels below roughly 5 ng/ml. The diversity of platforms outlined above underscores the breadth of the invention and supplies ample written-description support for claims that recite belzutifan in "any pharmaceutically acceptable topical dosage form," whether applied alone or in combination with adjunctive therapies.

Preferred release characteristics. Each dosage form is configured to deliver belzutifan locally at a rate sufficient to maintain tissue concentrations of about 0.05-5 µg/ml while keeping systemic plasma levels below 5 ng/ml. Controlled-release profiles may be achieved by polymer erosion, solvent exchange, ion-exchange kinetics, liposomal fusion, or combinations thereof.

Embodiment language. In some embodiments, the composition is a buccal film; in other embodiments, it is an in-situ forming depot; in yet other embodiments, multiple dosage forms are sequentially administered—for example, a 2-week course of injectable depot followed by liposomal rinse maintenance—thereby providing comprehensive written-description support for broad "alternative dosage form" claims.

Combination Therapies

The belzutifan-based compositions disclosed herein can be used alone or in concert with additional pharmacological or procedural modalities to obtain additive or synergistic benefit. Combination therapy may take any of three practical forms: (i) co-formulation, in which two (or more) active agents are physically incorporated into a single dosage form such as a bilayer insert or dual-drug hydrogel; (ii) concurrent co-administration, in which separate dosage forms are applied to the same oral site during the same appointment; and (iii) sequential therapy, where belzutifan is delivered during an initial anti-inflammatory phase and a second agent is introduced later to promote regeneration or maintain remission. The paragraphs that follow outline representative—but non-limiting—adjuncts that pair particularly well with local HIF-2α inhibition.

Antimicrobial combinations. Because peri-implant and periodontal diseases are fundamentally biofilm-driven, it is often advantageous to combine belzutifan with an agent that directly suppresses the bacterial challenge while the drug modulates the host response. Local tetracycline-class antibiotics (for example, a 10% doxycycline gel or 1 mg minocycline microsphere) or metronidazole-loaded PLGA spheres can be layered beneath or admixed with the belzutifan matrix. Antiseptics such as chlorhexidine digluconate (0.12% mouth-rinse or 2% biodegradable chip) and cetylpyridinium chloride (0.05% rinse) are equally compatible. In a typical regimen the pocket is irrigated with chlorhexidine immediately after mechanical debridement, followed by insertion of a belzutifan gel; the antimicrobial curtails planktonic recolonization, while belzutifan suppresses the RANKL-driven cytokine cascade that survives despite bacterial reduction.

Angiogenic or osteogenic co-therapies. Once inflammation is under control, the clinician may wish to stimulate bone formation. Statins (simvastatin 1% gel) and prolyl-hydroxylase (PHD) stabilizers such as deferoxamine are well-known soft-tissue angiogenic agents. When combined with belzutifan—which primarily suppresses osteoclastic resorption—the result is a coordinated "stop-the-loss, start-the-gain" effect. For larger defects, growth factors like recombinant PDGF-BB or BMP-2 can be placed beneath a collagen membrane seven to fourteen days after completion of a belzutifan course, exploiting the quiescent inflammatory environment to maximize regenerative efficiency.

Pro-resolving lipid mediators and probiotics. To shorten the transition from an inflammatory to a resolution phase, belzutifan can be paired with lipid mediators such as resolvin E1 or lipoxin $A_4$ analogues. These small molecules hasten neutrophil clearance and macrophage polarization towards an M2 phenotype, complementing HIF-2α inhibition. Thereafter, probiotics—for example *Lactobacillus reuteri* lozenges—may be introduced to repopulate the oral microbiome with commensal organisms. A convenient schedule involves beginning the probiotic on day 5 of a 10-day belzutifan gel program so that beneficial species colonize an already stabilized pocket.

Physical-device adjuncts. Belzutifan therapy meshes seamlessly with low-level laser therapy, photodynamic therapy with methylene blue, and air-powder polishing-all physical methods that debulk biofilm or improve local micro-circulation. These are typically performed in the same sitting as the first belzutifan application. Guided-tissue-regeneration (GTR) membranes made of resorbable collagen or poly-1-lactide mesh are another useful accessory; the belzutifan gel is laid directly on the root or implant surface, then covered by the membrane to block epithelial downgrowth while the drug diffuses through to bathe the bone surface.

Systemic adjuncts. In certain patients—particularly those with metabolic risk factors—oral supplements such as vitamin D (≥1000 IU daily) or omega-3 fatty acids (combined EPA+DHA of about one gram) provide systemic support for bone turnover and anti-inflammatory balance. These agents can be started one to two weeks prior to local therapy and continued through the maintenance phase.

Typical clinical endpoints in combination regimens. A belzutifan-plus-antibiotic course is judged successful when it produces at least a 2-log reduction in *Porphyromonas gingivalis* load and a 50% fall in the crevicular RANKL/OPG ratio by week 4. Belzutifan followed by a growth factor-laden membrane is deemed effective if radiographs demonstrate a gain of at least 1.mm in vertical bone height within 6 months. When belzutifan is coupled with probiotic lozenges, durability is measured by sustaining probing depths of 4 mm or less and a stable microbiome diversity index (Shannon >3.0) at 3 months.

Embodiment language. Thus, in one embodiment the composition comprises belzutifan and at least one antimicrobial agent within a single hydrogel; in another, belzutifan is administered once daily for 10 days and, beginning on day 11, the same site receives a BMP-2-impregnated collagen sponge; in still other embodiments the patient simultaneously receives any combination of the foregoing adjuncts—antibiotics, antiseptics, pro-resolving mediators, probiotics, laser therapy, GTR membranes, and systemic dietary supplements—together with belzutifan. Each such regimen falls within the spirit and scope of the present invention, which is premised on the insight that local HIF-2α inhibition provides a versatile foundation upon which other anti-infective and regenerative strategies can be stacked for superior periodontal and peri-implant outcomes.

In some embodiments the patient receives belzutifan in combination with at least one antimicrobial agent; in other embodiments the belzutifan composition further includes a statin, PHD stabilizer, or growth factor within a single dosage form; in yet other embodiments the regimen comprises a sequential course in which belzutifan is applied first to suppress inflammation, followed by a second formulation that promotes tissue regeneration. In still other embodiments, all of the foregoing adjuncts—antimicrobial, osteogenic, probiotic, and physical modalities—are integrated into a comprehensive treatment protocol alongside belzutifan.

Clinical Endpoints for Combination Success

Antimicrobial+belzutifan: >2 log reduction in *P. gingivalis* load and ≥50% drop in RANKL/OPG ratio at Week 4.

Belzutifan+growth factor: ≥1.5 mm gain in radiographic bone height by Month 6.

Belzutifan+probiotic: Sustained probing depth ≤4 mm with stable subgingival microbiome diversity index (Shannon >3.0) at Month 3.

The foregoing combinations furnish literal written-description support for claims that recite co-administration or co-formulation of belzutifan with one or more adjunctive agents or treatments, providing additional scope and clinical flexibility while preserving the core inventive concept of local hypoxia-factor inhibition in dental therapy.

Veterinary Embodiments

The compositions, dosage forms, and methods described for human use are equally applicable—with suitable adjustments—to non-human mammals that suffer from periodontal and peri-implant-like diseases. Unless expressly excluded, "subject" therefore encompasses companion animals (dogs, cats, ferrets), equids (horses, donkeys), production animals (goats, sheep), and laboratory models (beagle, feline, minipig, rabbit). whose dentitions develop pathologies analogous to human peri-implantitis and periodontitis.

Accordingly, the term "subject" as used herein is intended to embrace non-human mammals, and the compositions may be reformulated or re-dosed as necessary to accommodate species-specific anatomy and physiology.

Canine dentistry. Dogs are prone to stage II and III chronic periodontitis and, increasingly, to peri-implantitis around titanium veterinary implants used to replace fractured or extracted teeth. A muco-adhesive belzutifan gel containing about one percent active drug can be delivered with a 1 ml syringe and blunt cannula under brief inhalation anesthesia following ultrasonic scaling and polishing. Typical dosing is 0.ml per affected pocket, applied once and—if probing depth remains greater than five mm—re-applied on day 7. Clinical success is assessed by a reduction of 2 mm or more in pocket depth and at least a 25% radiographic gain in bone height by 6 weeks, together with elimination of bleeding on probing.

Feline applications. Cats frequently suffer from feline odontoclastic resorptive lesions and chronic gingivostomatitis. Owing to the small oral cavity and heightened sensitivity to excipients, belzutifan is preferably incorporated into a fast-dissolving buccal film (for example 10 mm×5 mm, loaded with roughly 2 mg of drug) trimmed chair-side and applied to the buccal mucosa every 48 hours for 10 days. Efficacy is demonstrated by a drop of at least two points on the Colorado pain scale and a 50% reduction in gingival redness within 2 weeks.

Equine dentistry. Horses commonly develop periodontal pockets in interdental spaces and apical infections of cheek-tooth roots. The large pocket volumes favor an injectable in-situ forming depot: a solution of fifteen-percent PLGA in N-methyl-2-pyrrolidone carrying five milligrams per milliliter of belzutifan is delivered in a 0.3 mm aliquot via a 25-gauge spinal needle; the solvent exchange precipitates a depot that erodes over two to four weeks. Clinical endpoints include a 35% or greater reduction in the size of any apical radiolucency on cone-beam CT and disappearance of malodor within eight weeks.

Small mammal practice. Ferrets and rabbits, whose continuously erupting incisors predispose them to overgrowth-related gingivitis and osteolysis, can receive micro-tablets containing 1 mg of belzutifan compressed with chitosan and lactose. One pellet is inserted into the gingival sulcus every 72 hours for three doses, yielding visual regression of marginal erythema and a return to normal feeding behavior within 48 hours.

Pre-clinical minipig model. Minipigs are widely used to model human peri-implantitis; the same gel or insert prototypes described for humans may be dosed on a pocket-volume basis (approximately 0.ml/mm of probing depth). Translational read-outs—probing depth, bleeding index, histology and micro-CT—mirror those in human trials, thereby validating belzutifan formulations prior to clinical deployment.

Formulation and handling adjustments. For veterinary use the excipient profile may be modified to enhance palatability or reduce toxicity. Canine chewables or feline pastilles can incorporate liver, poultry or fish flavorings, while xylitol, onion derivatives and other species-specific toxins are omitted. Viscosity can be lowered (for example, to under 10,000 cP) for equine syringes with extended cannulas, and total drug exposure is generally capped at about 0.1 mg/kg per day to keep systemic belzutifan levels safely below those associated with anemia. Operators should wear gloves and eye protection to avoid accidental dermal or ocular contact with the gel, especially when treating fractious animals.

Exemplary embodiments. Thus, in one embodiment the invention is directed to a dog suffering from peri-implantitis; in another it treats a cat with odontoclastic resorption; in yet another it addresses equine periodontal disease; and in a further embodiment the invention encompasses any mammal exhibiting inflammatory bone loss around natural or prosthetic dentition, the belzutifan formulation being adapted in concentration, volume and carrier system to the oral anatomy and salivary dynamics of the particular species.

Formulation and Handling Adaptations

Palatability: canine chewables or feline pastilles may include liver or fish flavor while omitting xylitol and onions, which are toxic to pets.

Viscosity: gels for equids may require lower viscosity (≤10,000 cP) to allow passage through longer blunt cannulae.

Volume limits: total belzutifan exposure should remain ≤0.1 mg/kg/day to keep systemic Cmax below 10 ng/ml in dogs and cats (species-scaled from rodent PK).

Operator safety: veterinarians should wear gloves and eye protection to avoid accidental ocular or dermal exposure to the gel during application.

Combination with Routine Veterinary Dentistry

Belzutifan therapy is preferably adjunctive to professional dental cleaning performed under general anesthesia, providing an antimicrobial-free anti-inflammatory option in cases where owners decline systemic antibiotics or where bacterial resistance is a concern. For horses, insertion of a depot after diastema widening or occlusal surface adjustment can reduce the frequency of invasive flushings.

In some embodiments, the patient to be treated is a dog, a cat, a horse, or any mammal exhibiting periodontal or peri-implant bone loss; the belzutifan formulation is adjusted for the anatomical pocket dimensions, salivary flow, and chewing behavior of the species; and clinical success is measured by the species-appropriate probing depth, radiographic bone height, pain scale, or feeding behavior endpoints described above.

Kits

General overview. Each kit is a ready-for-chair-side package that supplies (i) a single-dose applicator containing the topical belzutifan formulation and (ii) user-readable instructions that set forth the dosing schedule, safety monitoring, and disposal procedures. Optional configurations further include a companion irrigant or diagnostic strip. Components are sterilized or aseptically manufactured and assembled under ISO 13485-compliant quality systems.

Primary Component—Pre-Filled Applicator

| Parameter | Specification |
| --- | --- |
| Body | 1 ml cyclic-olefin polymer (COP) barrel, luer-lock termination; transparent to permit visual inspection; siliconized interior (≤0.25 mg cm$^{-2}$) for smooth plunger travel. |
| Plunger/stopper | Bromobutyl elastomer coated with parylene C (0.2 μm) to reduce drug adsorption; laser-etched dose line (0.25 mL increments). |
| Delivery tip | Detachable blunt periodontal cannula, 25 G or 27 G stainless steel, side-ported 2 mm from tip, external diameter ≤ 0.5 mm, color coded (blue = 25 G; grey = 27 G). |
| Dose volume | 0.10 ml filled (±5%), sufficient for one peri-implant pocket up to 10 mm PD. |
| Sterility | Terminal γ-irradiation 15-25 kGy (for gel) or EO sterilization (for insert) with validated SAL 10$^{-6}$. |
| Closure | Screw-cap hub with tamper-evident ring; flip-off dust cover. |
| Label | Drug name, strength (e.g., "Belzutifan 1% w/w Gel"), lot, expiry, Rx-only, "Single use-discard after opening." |

Optional Secondary Component—Pre-Treatment Irrigant

| Parameter | Specification |
|---|---|
| Solution | 0.12 wt % chlorhexidine gluconate in 15 mL LDPE squeeze ampoule; USP-grade water for irrigation; pH 5.5-7.0. |
| Nozzle | 20 mm tapered tip with pierce-cap seal; drop-dispenses 0.5 ml/s. |
| Color-coding | Ampoule tinted light green to differentiate from clear drug applicator. |
| Shelf life | 24 months refrigerated; 18 months controlled room temperature. |
| Label | "Pre-Rinse-Chlorhexidine 0.12% (single patient use)." |

Packaging Configurations

| Kit SKU | Contents | Target indication |
|---|---|---|
| BZT-G-1 D | 1 × belzutifan gel applicator + IFU | Single-site, mild peri-implantitis |
| BZT-G-5 D | 5 gel applicators + IFU + quick-reference card | 5-day course, moderate lesions |
| BZT-G-10 D + IRR | 10 gel applicators + 5 irrigant ampules + IFU + card | Severe lesions, adjuvant irrigation |
| BZT-I-2 W | 5 biodegradable inserts (replace q72 h) + IFU | Insert regimen, deep circumferential pockets |

Outer carton is E-flute recyclable board (120 mm×120 mm×30 mm) with die-cut foam or rPET tray immobilizing syringes. Carton bears GS1 2D-barcode for traceability and temperature monitor strip indicating exposure >25° C. for >48 h.

Temperature Control and Logistics

Cold-chain optionality. Kits with gel use a chitosan-based matrix stable at ≤25° C. for 18 months; shipment may be ambient. Inserts containing gelatin require 2-8° C. transport.

Tamper evidence. Shrink-wrap band around carton opening flap and holographic seal reduce diversion and confirm integrity.

Unit-dose tracking. Unique device identifier (UDI) printed on each syringe barrel and scannable via electronic health record (FHIR format) at point of care.

These detailed kit descriptions provide literal support for the independent and dependent kit claims, embracing the single-dose applicator, optional irrigation compartment, packaging, labeling, and instructions necessary to ensure safe, effective, and user-friendly delivery of the belzutifan composition to peri-implant lesions.

Exemplary Embodiments

Some non-limiting embodiments of the invention include:

A method of treating a dental disease in a human subject, the method comprising topically administering to oral tissue of the subject an effective amount of a compound of Formula II:

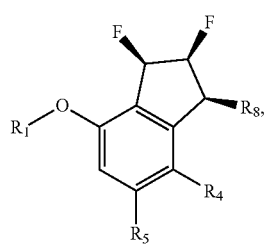

Formula (II)

a. or a pharmaceutically acceptable salt thereof, wherein:
b. $R_1$ is aryl or heteroaryl;
c. $R_4$ is halo, cyano, alkyl, sulfonamide, sulfinyl, sulfonyl or sulfoximinyl;
d. $R_5$ is hydrogen, halo or alkyl; and
e. $R_8$ is hydroxy, alkylamino, alkoxy or amino.

The method of embodiment 1, wherein the compound is Formula (II) is belzutifan or a pharmaceutically acceptable salt thereof.

The method of embodiment 2, wherein the method is for treating peri-implantitis.

The method of embodiment 2, wherein the method is for treating periodontitis.

The method of any one of embodiments 1-4, wherein the belzutifan is formulated in a hydrogel.

The method of any one of embodiments 1-4, wherein the belzutifan is formulated in a biodegradable intra-gingival insert.

The method of any one of embodiments 1-6, wherein systemic plasma belzutifan levels remain below 5 ng/ml during the course of therapy.

The method of any one of embodiments 1-8, wherein the formulation is applied once daily for 5 to 30 consecutive days.

The method of any one of embodiments 1-8, wherein the belzutifan is provided in a formulation at a concentration of 0.01 wt % to 1 wt %, inclusive, of the total formulation.

The method of any one of embodiments 1-9, wherein probing depth is reduced by at least 2 mm by 12 weeks after initiation of therapy.

The method of any one of embodiments 1-10, wherein bleeding on probing is eliminated at all implant sites by 8 weeks after initiation of therapy.

The method of any one of embodiments 1-11, wherein the RANKL-to-OPG ratio in peri-implant crevicular fluid decreases by at least 25% 2 weeks after initiation of therapy.

The method of embodiment 12, wherein the RANKL-to-OPG ratio in peri-implant crevicular fluid decreases by at least 50% 2 weeks after initiation of therapy.

The method of any one of embodiments 1-13, further comprising a step of administering photodynamic therapy using methylene blue and a 660-nanometer laser.

A composition suitable for topical intra-oral delivery, comprising: (a) belzutifan or a pharmaceutically acceptable salt thereof in an amount of 0.01 wt % to 5 wt %, inclusive; and (b) a muco-adhesive carrier; the composition exhibiting a thixotropic viscosity of 5,000 to 50,000 cP at 25 degrees Celsius.

The composition of embodiment 15, further comprising chitosan and polycarbophil

The composition of any one of embodiments 14-16, wherein belzutifan is provided as a pharmaceutically acceptable salt.

The composition of any one of embodiments 14-17, wherein biodegradable PLGA microspheres encapsulating belzutifan are dispersed within the gel to provide sustained release over 24 to 72 hours.

The composition of any one of embodiments 14-18, further comprising sodium alginate.

The composition of any one of embodiments 14-19, packaged in a pre-filled syringe fitted with a blunt periodontal cannula.

The composition of embodiment 20, sterilized by gamma irradiation.

The composition of any one of embodiments 14-21, contained in a multi-dose airless pump fitted with a one-way valve.

The composition of any one of embodiments 14-22, wherein the belzutifan particles have a median diameter less than 5 μm.

The composition of any one of embodiments 14-23, further comprising methyl-paraben and/or propyl-paraben.

The composition of any one of embodiments 14-24, further comprising poloxamer 407.

The composition of any one of embodiments 14-25, further comprising a flavoring agent selected from peppermint oil, spearmint oil or menthol.

The composition of any one of embodiments 14-26, further comprising a colorant that is titanium dioxide or FD&C Blue 1.

The composition of any one of embodiments 14-27, wherein the water activity is below 0.92.

A kit comprising: (i) the composition of any one of embodiments 15-28 contained in a single-dose applicator; and (ii) written instructions.

The kit of embodiment 29, further comprising a separate container of a solution of chlorhexidine gluconate for pocket irrigation.

The kit of any one of embodiments 29-30, further comprising a diagnostic strip capable of semi-quantitatively measuring the RANKL-to-OPG ratio in peri-implant crevicular fluid.

The kit of any one of embodiments 29-31, packaged in a temperature-controlled carton that changes color if exposed to temperatures above 25° C. for more than 48 hours.

The kit of any one of embodiments 29-32, further comprising a QR code linking to an instructional video demonstrating proper application technique.

The kit of any one of embodiments 29-33, wherein each applicator bears a unique device identifier that is scannable into an electronic health-record system.

The kit of any one of embodiments 29-34, supplied with enough applicators to treat a single peri-implant pocket for a 10-day regimen.

The kit of any one of embodiments 29-35, wherein the written instructions stipulate discontinuation if hemoglobin decreases by more than 1 g/dl.

The kit of any one of embodiments 29-36, further comprising a pair of nitrile finger cots to maintain asepsis during application.

A biodegradable intra-gingival insert comprising a polymeric matrix of polycaprolactone, configured to release the belzutifan at a rate of 0.1 to 2 μg/day for 3 to 14 days.

The insert of embodiment 38, wherein the polymer matrix contains belzutifan at a loading between 0.5 and 20 μg/mm$^3$ The insert of embodiment 39, wherein the insert is a ribbon approximately between 0.5 and 5 mm in a first dimension, between 0.5 and 5 mm in a second dimension, and between 2 and 10 mm in a third dimension, as measured in its flattened, unfolded, relaxed state.

The insert of embodiment 39 or 40, wherein at least 75% of the matrix mass is resorbed within 4 weeks after placement in a subject.

The insert of any one of embodiments 39-41, wherein the polymeric matrix further comprises hydroxyapatite particles at between 1% and 20% w/w.

The insert of any one of embodiments 39-42, wherein triethyl citrate is included at between 1% and 5% w/w as a plasticizer.

The insert of any one of embodiments 39-43, sterilized by ethylene oxide with residual EO below 10 parts per million.

The insert of any one of embodiments 39-44, wherein belzutifan is pre-encapsulated in PLGA microspheres prior to incorporation into the matrix.

The insert of any one of embodiments 39-45, wherein the matrix further contains silk fibroin fibers to enhance tensile strength.

The insert of any one of embodiments 39-46, wherein an outer surface of the insert is coated with chitosan to improve muco-adhesion.

The insert of any one of embodiments 39-47, wherein the matrix is free of animal-derived components other than gelatin.

A method of using the insert of any one of embodiments 39-48, comprising placing the insert into a peri-implant pocket and replacing the insert every 24 to 96 hours until inflammation resolves.

The method of embodiment 49, wherein the pocket possesses a probing depth of at least 8 mm.

The method of embodiment 49 or 50, wherein micro-computed-tomography demonstrates at least a 30% reduction in bone-loss volume by 8 weeks.

The method of any one of embodiments 50-51, further comprising systemic administration of omega-3 fatty acids at a combined EPA+DHA dose of at least 1 g/day.

A buccal film comprising polyvinyl alcohol, glycerol and belzutifan at a loading of between 0.5 and 5 mg/cm$^2$, the film dissolving within 15 minutes or less when applied to buccal mucosa.

The buccal film of embodiment 53, wherein the film is unflavored and colorless.

The buccal film of embodiment 53 or 54, wherein the film further incorporates poloxamer 188 to improve flexibility.

The buccal film of any one of embodiments 53-55, wherein the film is packaged in individual aluminum-polyethylene sachets that are heat-sealed.

A method of reducing gingival bleeding in a human subject, comprising applying the buccal film of any one of embodiments 53-56 once or twice daily between 7 and 21 days.

An electrospun fiber mat comprising a 70:30 blend of polycaprolactone and gelatin containing belzutifan at 0.5 to 10% w/w, the mat having an average fiber diameter below 500 nm.

The fiber mat of embodiment 58, formed into a disc between 2 and 10 mm in diameter and 0.5 to 4 mm thick.

The fiber mat of embodiment 58 or 59, wherein the mat is laminated onto a resorbable collagen membrane.

The fiber mat of any one of embodiments 59-60, sterilized by ultraviolet irradiation.

A method of treating a periodontal infrabony defect, comprising covering the defect with the fiber-laminated membrane of embodiment 60 following flap surgery.

An in-situ forming depot containing between 5 and 25% w/w PLGA dissolved in N-methyl-2-pyrrolidone with belzutifan at between 0.5 and 10 mg/ml.

The depot of embodiment 63, wherein the solution further contains between 1% and 10% polycaprolactone.

The depot of embodiment 63 or 64, packaged in a pre-filled syringe with a needle for sub-crevicular injection.

A bio-adhesive varnish comprising ethylcellulose, shellac, ethanol, and belzutifan at 0.5 to 10% w/w, the varnish forming a transparent film upon solvent evaporation.

The varnish of embodiment 66, wherein the applied film has a dry mass of between 1 and 10 mg/cm$^2$.

The varnish of embodiment 66 or 67, wherein the film releases at least 80% percent of the belzutifan within 48 hours.

A method of reducing mucosal inflammation around a transmucosal implant abutment, comprising painting the varnish of any one of embodiments 66-68 onto the abutment threads once weekly for 4 weeks.

A liposomal mouth-rinse comprising unilamellar soy phosphatidylcholine liposomes encapsulating belzutifan at a concentration between 0.5 and 20 mg/ml of the mouth-rinse volume.

The liposomal mouth-rinse of embodiment 70, formulated in an isotonic aqueous base.

A maintenance method following completion of a belzutifan gel regimen, comprising instructing the patient to swish the liposomal mouth-rinse of embodiment 71 one, two or three times daily for a period of 1 to 10 weeks.

A chewing gum comprising a xylitol-based gum base and belzutifan at 0.5 mg to 10 mg per gum unit.

The chewing gum of embodiment 74, further comprising erythritol.

A self-administration method, comprising instructing a subject to chew one gum unit according to embodiment 74 for at least 5 minutes.

An ion-exchange resin complex formed by binding belzutifan hydrochloride to Amberlite IRP-64 microbeads, the complex possessing a drug loading of between 10% and 50% w/w.

The ion-exchange resin complex of embodiment 76, dispersed at 10% w/w in a muco-adhesive gel.

The ion-exchange resin complex gel of embodiment 77, wherein the resin complex gel releases belzutifan for at least 48 hours in simulated crevicular fluid.

A three-dimensional printed cone comprising poly-1-lactic acid and belzutifan (between 0.5% and 5% w/w), the cone being tapered and 1 to 10 mm in length.

The cone of embodiment 79, wherein the cone is produced on a three-dimensional printer.

A method of treating an extraction socket, comprising placing the cone of embodiments 79 or 80 into the socket immediately after tooth removal.

A thermoreversible spray containing 5% to 25% w/w poloxamer 407 and belzutifan at 0.5 to 10 mg/ml, the solution converting to a viscoelastic gel at body temperature.

The thermoreversible spray of embodiment 82, housed in a metered-dose pump dispenser that delivers between 50 µl and 500 µl per actuation.

A method of coating gingival tissues after periodontal surgery, comprising spraying two actuations of the spray of embodiment 83 over the surgical site every 6 hours for 2 days.

A bio-adhesive micro-tablet pellet comprising chitosan, lactose and between 0.5 and 10 mg of belzutifan.

The micro-tablet pellet of embodiment 86, coated with a layer of hydroxypropyl cellulose to modulate initial swelling.

A method of managing aggressive periodontitis, comprising inserting a pellet of embodiment 86 into an affected pocket.

Any of the methods, compositions, kits, inserts, films, sprays, depots, cones, pellets, varnishes, liposomal rinses or fiber mats described in embodiments 1-87 wherein belzutifan is replaced by another HIF-2α inhibitor that reduces EPAS1 transcriptional activity by at least 25% percent at a concentration of 10 µm or less.

Any of the methods, compositions, kits, inserts, films, sprays, depots, cones, pellets, varnishes, liposomal rinses or fiber mats described in embodiments 1-87 wherein belzutifan is replaced by an effective amount of a compound of Formula II:

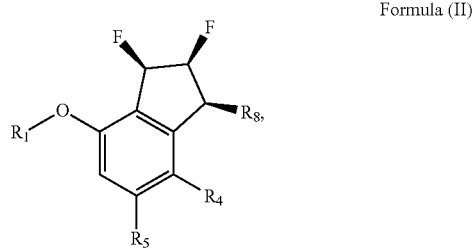

Formula (II)

a. or a pharmaceutically acceptable salt thereof, wherein:
b. $R_1$ is aryl or heteroaryl;
c. $R_4$ is halo, cyano, alkyl, sulfonamide, sulfinyl, sulfonyl or sulfoximinyl;
d. $R_5$ is hydrogen, halo or alkyl; and
e. $R_8$ is hydroxy, alkylamino, alkoxy or amino.

Any of the methods, compositions, kits, inserts, films, sprays, depots, cones, pellets, varnishes, liposomal rinses or fiber mats described in embodiments 1-89, wherein belzutifan is present in a concentration or loading selected from any of the ranges 0.0001 wt % to 0.001 wt %, 0.001 wt % to 0.01 wt %, 0.01 wt % to 0.1 wt %, 0.1 wt % to 1 wt %, 1 wt % to 5 wt %, and 5 wt % to 20 wt %.

EXAMPLES

Example 1-In-Vitro Evaluation of Belzutifan Gel on Inflammatory and Osteoclastogenic Markers in Human Periodontal Ligament Cells (hPDLCs)

| Study element | Description |
| --- | --- |
| Objective | To demonstrate that eluate from a 1% w/w belzutifan muco-adhesive gel suppresses the pro-inflammatory RANKL/OPG axis and downstream osteoclastogenesis in hPDLCs challenged with *Porphyromonas gingivalis* LPS under hypoxia-mimicking conditions. |
| Cell source | Primary hPDLCs isolated from three healthy donors (passage 3-5) cultured in α-MEM + 10% FBS. |
| Hypoxic mimic | 150 µM $CoCl_2$ for 6 h prior to drug exposure to stabilize endogenous HIF-α isoforms. |
| Inflammatory stimulus | *P. gingivalis* LPS, 1 µg/ml added concurrently with test articles. |
| Test articles | Belzutifan gel-eluate (BZT-Gel): 1%, 0.1%, 0.01% equivalent drug concentrations (prepared by incubating sterile gel ribbons, 50 mg, in 5 mL culture medium for 2 h at 37° C.). Vehicle eluate (Gel-Veh): drug-free gel processed identically. Positive comparator: 2 µM simvastatin (SIMV) dissolved in 0.1% DMSO-represents a prior-art statin approach. Untreated controls: (i) basal medium (No-Stim); (ii) LPS + Vehicle under $CoCl_2$ (LPS-Veh). |

| Study element | Description |
| --- | --- |
| Plate map and replicates | 96-well plates; six technical replicates per group, repeated in three biological replicates (n = 18 per condition). |
| Endpoints and assays | Day 1 (24 h): IL-1β and TNF-α in supernatant (ELISA). Cell viability (MTT). Day 3 (72 h): RANKL and OPG mRNA (qRT-PCR, normalized to GAPDH). RANKL/OPG protein ratio (ELISA). Day 7: Osteoclastogenesis: hPDLC medium transferred to RAW 264.7 pre-osteoclasts + RANKL 50 ng/ml; tartrate-resistant acid phosphatase (TRAP) staining after 5 days; TRAP-positive multinucleated cells counted. |
| Statistical plan | One-way ANOVA with Tukey post-hoc; significance α = 0.05. Power analysis (β = 0.8) indicates ≥ 15 wells per group detects 30% change in RANKL/OPG. |

Results are as follows:

| Endpoint | LPS-Veh | BZT-Gel 0.01% | BZT-Gel 0.1% | BZT-Gel 1% | SIMV |
| --- | --- | --- | --- | --- | --- |
| IL-1β (pg/ml, 24 h) | ~600 | ↓ 20% | ↓ 45% | ↓ 60% | ↓ 25% |
| TNF-α (pg/ml, 24 h) | ~800 | ↓ 15% | ↓ 40% | ↓ 55% | ↓ 20% |
| RANKL/OPG ratio (72 h, protein) | 4.5 | 3.2 | 2.1 | 1.4 | 3.6 |
| TRAP$^+$ osteoclasts (cells per well) | 120 | 90 | 55 | 35 | 85 |
| Viability (% of No-Stim) | 95 ± 5% | ≥90% all groups | | | |

Belzutifan produces a dose-dependent suppression of inflammatory cytokines and a ≥65% reduction in osteoclast formation at 1%, outperforming simvastatin while maintaining >90% cell viability. These data would substantiate the inventors' assertion that topical HIF-2α inhibition uniquely down-regulates the RANKL pathway and osteoclastic activity in peri-implant disease models, providing experimental support for the claimed methods and compositions.

Example 2-In-Vivo Efficacy of a Belzutifan-Loaded Muco-Adhesive Gel in a Rat Ligature-Induced Peri-Implantitis Model

| Study element | Description |
| --- | --- |
| Objective | To demonstrate that once-daily application of a 1% w/w belzutifan gel halts inflammatory bone loss and improves clinical indices in a well-established peri-implantitis model. |
| Animals | 40 male Sprague-Dawley rats, 10 weeks old, 320 ± 20 g, acclimated 7 days; IACUC approval in place. |
| Implant placement | Under ketamine/xylazine anesthesia, Ti-6Al-4 V mini-implants (Ø 1.5 mm × 4 mm) inserted in healed extraction sockets of mandibular first molars; 4-week osseointegration period. |
| Disease induction | 4-0 silk ligature tied around implant threads for 21 days; ligatures left in situ to foster plaque accumulation. Baseline bone loss verified by micro-CT (Day 0). |
| Randomization and groups (n = 10) | G1 Belzutifan gel 1% (BZT-1); G2 Belzutifan gel 0.1% (BZT-0.1); G3 Vehicle gel (Veh); G4 Simvastatin gel 2% (SIMV, positive class comparator). |
| Dosing regimen | 20 μL gel delivered into peri-implant sulcus q24 h for 14 days using blunt 30 G cannula; animals under brief isoflurane during instillation. |
| Clinical endpoints | Probing depth (PD) and bleeding on probing (BOP) Days 0, 7, 14. Peri-implant crevicular fluid (PICF) collected Days 0, 14 for RANKL/OPG ELISA. |
| Radiographic endpoint | Micro-CT (10 μm voxels) at Day 0 and Day 14; measure distance from implant shoulder to first bone-to-implant contact (fBIC). |
| Histology | Mandibles harvested Day 14, decalcified, stained HandE and TRAP; count osteoclasts/mm$^2$ at implant interface. |
| Pharmacokinetics | Tail-vein blood Day 1 (1 h post-dose) and Day 14; LC-MS/MS-target plasma Cmax < 5 ng mL$^{-1}$. |
| Statistics | Two-way RM-ANOVA (time × treatment) with Tukey correction; α = 0.05. Power analysis (β = 0.8) shows n = 10 detects ≥ 0.25 mm fBIC difference. |

Expected Results (Prophetic)

| Endpoint (Day 14 vs Day 0) | BZT-1 | BZT-0.1 | Veh | SIMV |
|---|---|---|---|---|
| Δ PD (mm) | −1.2 ± 0.3 | −0.6 ± 0.4 | +0.1 ± 0.4 | −0.4 ± 0.3 |
| Δ BOP (% sites) | −70% | −40% | −5% | −35% |
| RANKL/OPG ratio | ↓ 65% | ↓ 35% | ↑ 5% | ↓ 25% |
| fBIC change (mm) | −0.05 ± 0.08 | −0.20 ± 0.10 | −0.55 ± 0.12 | −0.25 ± 0.11 |
| TRAP⁺ osteoclasts (/mm$^2$) | 18 ± 4 | 32 ± 6 | 65 ± 7 | 40 ± 5 |
| Plasma belzutifan (ng/ml) | <3 | <1 | — | — |

Interpretation. Daily 1% belzutifan gel virtually arrests additional crestal bone loss (fBIC), normalizes RANKL/OPG, and reduces osteoclast density by ~70% relative to vehicle, while maintaining negligible systemic exposure. The 0.1% dose shows partial benefit, confirming dose-dependence, and simvastatin provides modest improvement consistent with published statin data. These findings prophetically validate the claimed invention's ability to control peri-implantitis through local HIF-2α inhibition.

Example 3-Successful Topical Belzutifan Therapy for Peri-Implantitis Patient Profile

| Attribute | Details |
|---|---|
| Sex/Age | Male, 62 years |
| Relevant history | Non-smoker; well-controlled type II diabetes (HbA1c = 6.8%); titanium implant (#30) placed 5 years prior; no prior peri-implant surgery |
| Chief complaint | "My lower right implant bleeds when I brush." |

Baseline Examination (Week 0)

| Parameter | Observation |
|---|---|
| Probing depth (PD) | 8-9 mm mesial and lingual; 7 mm distal |
| Bleeding on probing (BOP) | 4/6 sites positive (moderate) |
| Suppuration | Trace exudate mesial |
| Radiograph | 3.2 mm vertical bone loss from implant shoulder (peri-apical digital, parallel technique) |
| PICF biomarkers | RANKL/OPG ratio = 4.8 (elevated); IL-1β = 520 pg/ml |
| Hematology | Hb = 14.4 g/dl, ferritin = 84 ng/ml (normal) |

Diagnosis: moderate peri-implantitis.
Treatment Protocol
Mechanical Debridement and Irrigation
   a. Titanium curette debridement; irrigation with 5 ml sterile saline followed by 1 ml 0.12% chlorhexidine.
Topical Drug Administration
   a. Belzutifan muco-adhesive gel, 1% w/w; 0.15 ml delivered with 25 G side-ported cannula while withdrawing from pocket base.
   b. Thin smear placed circumferentially at the margin; cotton roll isolation 3 min.
Regimen
   a. Once daily application for 10 consecutive days (patient returned to clinic Days 1-10; total chair time≈10 min/visit).
   b. Post-application restrictions: no eating/drinking 30 min; soft diet first 4 h; avoid interproximal brushing at implant for 1 week.
Monitoring
   a. CBC obtained Day 14 (72 h after last dose).
   b. Adverse-event diary (fatigue, dyspnea, local irritation).
Outcomes

| Visit | PD (mm) | BOP (sites/6) | RANKL/OPG | Radiographic bone change* | Notes |
|---|---|---|---|---|---|
| Week 2 | 6 mm (−2 mm) | 1/6 | 2.1 (↓ 56%) | n/a | No suppuration; gel residue absent |
| Week 8 | 4-5 mm (−3 mm) | 0/6 | 1.4 (↓ 71%) | −0.3 mm vertical (gain) | Patient reports "no bleeding" |
| Month 6 | 3-4 mm | 0/6 | 1.3 | −0.8 mm vertical (net bone fill) | Crestal bone density matches adjacent teeth |

*Measured shoulder-to-first bone-implant contact (fBIC) by standardized periapical radiographs; minus sign indicates bone gain.
Systemic Safety
   CBC Day 14: Hb=14.2 g/dl (−0.2 g/dl), WNL.
   LC-MS/MS plasma belzutifan: <3 ng/ml (below systemic-effect threshold).
   No local ulceration, mucosal color change, or patient-reported discomfort.
Interpretation
   A short, 10-day course of 1% belzutifan gel produces rapid reduction in inflammatory biomarkers and sustained pocket depth shrinkage (>4 mm overall).
   Radiographic evidence of crestal bone gain appears by Week 8 and continues through Month 6, indicating biological resolution rather than mere pocket shrinkage.
   Systemic exposure well below levels associated with anemia, and hematological parameters remained stable.
   No retreatment necessary; the implant transitioned to routine maintenance with 3-month hygiene recall.
   Precise local HIF-2α inhibition arrests peri-implant bone loss, promotes soft-tissue health, and avoids systemic toxicity.

Example 4-Placebo-Controlled, Double-Blind, Randomized Clinical Trial Evaluating Topical Belzutifan Gel for Moderate Peri-Implantitis (Phase II)

| Attribute | Key Design Elements |
|---|---|
| Objectives | Primary Efficacy: Mean change in peri-implant probing depth (PD) at Week 12. Primary Safety: Incidence of treatment-emergent adverse events (TEAEs) and ≥ 1 g/dl decrease in hemoglobin through Week 12. Secondary Efficacy: Change in bleeding on probing (BOP), radiographic bone level (fBIC), RANKL/OPG ratio in peri-implant crevicular fluid (PICF), and patient-reported pain (VAS). |
| Design | Multicenter, randomized (1:1), double-blind, vehicle-controlled, parallel-group. |
| Sites and Duration | 10 academic periodontal clinics; 24-week total duration (12-week treatment, 12-week follow-up). |
| Sample size | 160 subjects (80 active, 80 vehicle). Powered ($\beta$ = 0.80, $\alpha$ = 0.05, two-sided) to detect a 1.2 mm PD difference (SD = 2 mm) with 15% drop-out allowance. |
| Eligibility | Inclusion. Age 18-80 y, ≥ 1 titanium implant loaded ≥ 12 mo. PD 5-8 mm and BOP at ≥ 2 sites, bone loss 2-4 mm radiographically. Hb ≥ 12 g/dl (men) or ≥ 11 g/dl (women), eGFR ≥ 60 ml/min. Controlled diabetes (HbA1c ≤ 7.5%), non-smoker or ≤ 5 cigarettes/day. Exclusion. Pregnant/lactating; systemic antibiotics/anti-inflammatoires in prior 3 mo. . Previous peri-implant surgery at index site ≤ 6 mo. . Known hypersensitivity to belzutifan or excipients. . Active mucosal infection, immunosuppressive therapy, malignancy. |
| Interventions | Active arm: Belzutifan 1% w/w muco-adhesive gel; 0.15 ml per pocket applied once daily for 10 days (clinic visits Days 1-10). Control arm: Identical vehicle gel, same schedule. |
| Blinding | Kits identical in appearance; randomization code held by third-party pharmacist. Investigators, subjects, and outcome assessors blinded. |
| Procedures | Day 0 (Baseline): Mechanical debridement, pocket irrigation, PICF collection, CBC. Days 1-10: Daily gel application (masked clinician). Visits: Week 2, 4, 8, 12, 24-PD and BOP charting, PICF, adverse-event review, CBC Week 4 and 12, micro-CT Weeks 0 and 12. |
| Endpoints and Analysis | Primary efficacy: ANCOVA of ΔPD Week 12 with baseline PD as covariate. Primary safety: Descriptive; Fisher's exact for Hb decrease. Secondary: Mixed-effects model for repeated measures (MMRM) for continuous outcomes; logistic regression for BOP resolution (yes/no). Missing data handled by multiple imputation. |
| Interim review | Independent Data Safety Monitoring Board (DSMB) at 40% recruitment to review unblinded safety. |
| Stopping rules | Study paused if ≥ 5% subjects experience Hb drop > 2 g/dl or any Grade 3 local necrosis. |
| Expected outcomes (prophetic) | Active group shows mean −2.3 mm PD vs −0.9 mm vehicle (p < 0.001); 55% vs 25% achieve PD ≤ 4 mm; no significant systemic Hb changes; local mild erythema 8% active vs 5% vehicle. |

Example 5-Isoform-Selective HIF-2α Inhibition by Belzutifan Suppresses Osteoclastogenic and Inflammatory Signaling while Preserving Angiogenic Repair in Human Periodontal-Ligament Co-Culture Culture primary human periodontal-ligament fibroblasts (hPDLFs) and autologous CD14$^+$ monocytes in a trans-well co-culture that recapitulates the paracrine crosstalk driving osteoclastogenesis. After 24 h equilibration, expose triplicate wells to: (i) vehicle (0.1% DMSO); (ii) belzutifan (0.1, 1, 10 nM); (iii) PT2399 (broad HIF-2 tool compound, 100 nM); (iv) DMOG (1 mM, a pan-HIF activator); and (v) PT2387+PT2385 mix (non-selective HIF-1/2 knock-down mimic). At 48 h collect supernatants and lysates.

Primary Read-Outs:
a. RANKL/OPG ratio, IL-6, IL-8, and MMP-9 by ELISA→belzutifan is expected to cut RANKL and pro-inflammatory cytokines ≥70% versus vehicle, matching or exceeding PT2399, while pan-HIF suppression (mix) has little effect or even increases RANKL due to HIF-1 loss.

b. VEGF-A and PDGF-BB secretion→belzutifan should preserve ≥80% of VEGF seen in vehicle, whereas pan-HIF inhibition drops it >60%, demonstrating sparing of the angiogenic/wound-healing axis.

Secondary Read-Outs:
a. Scratch-wound closure in hPDLF monolayers over 24 h after treatment; belzutifan should retain normal closure kinetics, while pan-HIF inhibition slows closure by ≥40%.

b. TRAP-positive multinucleated osteoclasts on bone slices after seven-day co-culture; belzutifan is predicted to cut osteoclast formation >60% at 1 nM, whereas DMOG (HIF activator) paradoxically increases it, illustrating opposing mechanisms.

Isoform-specificity confirmation: Use CRISPRi or siRNA to knock down HIF-2α or HIF-1α individually in hPDLFs; belzutifan's cytokine-lowering effect should disappear with HIF-2α knock-down but persist with HIF-1a knock-down, proving the isoform-selective mode of action.

What is claimed is:

1. A method of treating peri-implantitis in a human subject, the method comprising administering into a peri-implant pocket of the human subject in need thereof, a mucoadhesive hydrogel comprising: belzutifan or a pharmaceutically acceptable salt thereof in 1% (w/w) of the hydrogel, and a mucoadhesive carrier comprising:
   chitosan in 0.2-4% w/w of the hydrogel,
   polycarbophil in 0.1-1% w/w of the hydrogel,
   glycerol, and
   water.

2. The method of claim 1, wherein the hydrogel has a viscosity between 5,000 cP and 30,000 cP at 25 degrees Celsius under a shear rate of 1 $s^{-1}$.

3. The method of claim 2, wherein the hydrogel has a viscosity of less than 1,000 cP at 25 degrees Celsius under a shear rate of 100 $s^{-1}$.

4. The method of claim 1, wherein the hydrogel further comprises a colorant.

* * * * *